United States Patent
Münzer

(10) Patent No.: US 10,871,448 B2
(45) Date of Patent: Dec. 22, 2020

(54) FLUORESCENCE LIFETIME SENSOR MODULE AND METHOD OF DETERMINING A FLUORESCENCE LIFETIME USING A SENSOR MODULE

(71) Applicant: ams AG, Premstätten (AT)

(72) Inventor: Martin Münzer, St. Katharein (AT)

(73) Assignee: AMS AG, Premstätte N (AT)

( * ) Notice: Subject to any disclaimer, the term of this patent is extended or adjusted under 35 U.S.C. 154(b) by 27 days.

(21) Appl. No.: 16/338,934

(22) PCT Filed: Oct. 4, 2017

(86) PCT No.: PCT/EP2017/075191
§ 371 (c)(1),
(2) Date: Apr. 2, 2019

(87) PCT Pub. No.: WO2018/065456
PCT Pub. Date: Apr. 12, 2018

(65) Prior Publication Data
US 2020/0041414 A1    Feb. 6, 2020

(30) Foreign Application Priority Data
Oct. 4, 2016    (EP) .................................... 16192198

(51) Int. Cl.
*G01N 21/64*    (2006.01)

(52) U.S. Cl.
CPC . *G01N 21/6408* (2013.01); *G01N 2021/6471* (2013.01); *G01N 2021/6478* (2013.01);
(Continued)

(58) Field of Classification Search
CPC ....... G01N 21/6408; G01N 2021/6471; G01N 2021/6478; G01N 2201/0612;
(Continued)

(56) References Cited

U.S. PATENT DOCUMENTS 7,117,098 B1 * 10/2006 Dunlay .............. G01N 21/6428
702/21
2015/0131094 A1 * 5/2015 Alquaity ................ G01N 21/39
356/326

(Continued)

FOREIGN PATENT DOCUMENTS

| EP | 1674856 | 6/2006 |
|---|---|---|
| EP | 2347703 | 7/2011 |
| WO | 2015/136100 | 9/2015 |

OTHER PUBLICATIONS

Li et al., "Compact algorithmic time-to-flight converter," 2015, Electronics Letter, vol. 51, No. 3, pp. 213-215. (Year: 2015).*

(Continued)

*Primary Examiner* — Kiho Kim
(74) *Attorney, Agent, or Firm* — MH2 Technology Law Group LLP

(57) ABSTRACT

A fluorescence lifetime sensor module comprises an opaque housing having a first chamber and a second chamber which are separated by a light barrier. An optical emitter is arranged in the first chamber and configured to emit through a first aperture. Emission of pulses of light of a specified wavelength is arranged to optically excite a fluorescent probe to be positioned in front of the sensor module. A detector is arranged in the second chamber and configured to detect through a second aperture received photons from the fluorescent probe. A measurement block is configured to determine respective difference values representative of an arrival time of one of the received photons with respect to the emission pulses. A histogram block is configured to accumulate the difference values in a histogram. A processing circuit is configured to compute time-of-flight values based on an evaluation of the histogram, compute a fluorescence lifetime from the time-of-flight values and generate an output signal being indicative of the fluorescence lifetime (Continued)

of the fluorescent probe. A control unit is configured to initiate pulsed emission of the optical emitter.

15 Claims, 3 Drawing Sheets

(52) U.S. Cl.
CPC ............ *G01N 2201/0612* (2013.01); *G01N 2201/0697* (2013.01); *G01N 2201/105* (2013.01)

(58) Field of Classification Search
CPC ..... G01N 2201/0697; G01N 2201/105; G01N 21/6458; G01N 2201/0221; G01N 2201/0228; G01N 2201/024; G01N 21/6456; G01N 2201/0222; A61B 5/0071
See application file for complete search history.

(56) References Cited

U.S. PATENT DOCUMENTS

| | | |
|---|---|---|
| 2015/0173621 A1 | 6/2015 | Guo et al. |
| 2016/0033413 A1* | 2/2016 | Chodavarapu ..... G01N 21/6456 435/288.7 |
| 2016/0041095 A1 | 2/2016 | Rothberg et al. |
| 2016/0133668 A1 | 5/2016 | Rothberg et al. |

OTHER PUBLICATIONS

Vornicu et al., "A CMOS 0.18 micron 64 x 64 single photon image sensor with in-pixel 11b time-to-digital converter," 2014, IEEE 2014 International Semiconductor conference pp. 131-134. (Year: 2014).*

Esposito, Alessandro, "Beyond Range: Innovating Fluorescence Microscopy", *Remote Sensing*, vol. 4, No. 4, pp. 111-119 (Jan. 5, 2012).

Bhandari, A. et al.: "Blind and reference-free fluorescence lifetime estimation via consumer time-of-flight sensors" OPTICA, vol. 2, No. 11, Nov. 10, 2015, p. 965-973.

European Patent Office, International Search Report for PCT/EP2017/075191 dated Nov. 21, 2017.

Pifferi, A. et al.: "New frontiers in time-domain diffuse optics, a review" Journal of Biomedical Optics, SPIE, vol. 21, No. 9, Sep. 2016, 091310.

Villa, F. et al.: "CMOS Imager With 1024 SPADs and TDCs for Single-Photon Timing and 3-D Time-of-Flight" IEEE Journal of Selected Topics in Quantum Electronics, vol. 20, No. 6, Nov./Dec. 2014.

* cited by examiner

FLUORESCENCE LIFETIME SENSOR MODULE AND METHOD OF DETERMINING A FLUORESCENCE LIFETIME USING A SENSOR MODULE

This invention relates to a fluorescence lifetime sensor module and to a method of determining a fluorescence lifetime using a sensor module.

BACKGROUND OF THE INVENTION

Fluorescence-based analysis is a fundamental tool in basic research and development. Detection of fluorescence allows unprecedented insight into minute changes in the nanosecond lived electronic states of fluorescent molecules and their immediate neighborhood. In fluorescence analysis light is detected which has been emitted by fluorophores. Such a fluorophore, or fluorescent molecule, can be optically excited with light of an appropriate wavelength. In turn, the molecule undergoes various radiative or non-radiative internal transitions to an electronic excited state and then decays back to its ground state by emitting a photon at a longer wavelength. This decay is random in nature and can be characterized by a decay rate or fluorescence lifetime. Fluorescence lifetime is a specific characteristic of particular fluorescent probe. However, lifetimes are also sensitive to the immediate physical and chemical neighborhood of a molecule. Thus, determining fluorescence lifetime permits identification of specific, probe derived signals and their separation from on specific background fluorescence.

The average time a fluorophore spends in its excited state is in the nanosecond range for many fluorophores. Modern fluorescence setups make use of electronics that is able to provide the time resolution necessary to determine lifetime with high accuracy. For example, single photon avalanche diode arrays provide high sensitivity and allow detection down to single photons. Sensor signals provided by these types of detectors are analyzed by the principles of time correlated single photon counting (TCSPC), for example. However, current fluorescence lifetime analysis equipment tends to be bulky, sensitive to optical misalignment and expensive. Thus, typical application of fluorescence principles is restricted to research laboratories.

SUMMARY OF THE INVENTION

It is to be understood that any feature described in relation to any one embodiment may be used alone, or in combination with other features described hereinafter, and may also be used in combination with one or more features of any other of the embodiments, or any combination of any other of the embodiments, unless explicitly described as an alternative. Furthermore, equivalents and modifications not described below may also be employed without departing from the scope of the fluorescence lifetime sensor module and the method of determining a fluorescence lifetime using a sensor module as defined in the accompanying claims.

In at least one embodiment a fluorescence lifetime sensor module comprises an opaque housing having a first chamber and a second chamber. The chambers are separated by a light barrier arranged in the housing. The sensor module further comprises an optical emitter and a detector. The light barrier is arranged to block light, e.g. direct emission from the optical emitter, from reaching the detector.

The housing comprises a mold material or otherwise optically opaque material, for example. The term "optically opaque" refers to an opacity to electromagnetic radiation, such as light with a specified wavelength within an emission wavelength range of the optical emitter. "Opaque" may further include opacity for infrared, visible and/or ultraviolet radiation, for example. Generally, hereinafter the expression "light" refers to electromagnetic radiation in the visible, infrared and ultraviolet spectrum, if not stated otherwise. Typically, the material of the housing is opaque with respect to the emission of the optical emitter and emission from the fluorescent probe. The term "specified wavelength" denotes a known excitation wavelength which is used during a fluorescence experiment. For example, the optical emitter may have one or more emission lines. The specific wavelength used to excite the probe is then denoted "specified wavelength". Similarly, in case the optical emitter is tunable within a continuous or discrete a range of wavelength, the wavelength used to excite the fluorescent probe is also denoted "specified wavelength".

Furthermore, the first and second chambers are translucent or transparent at least for light with a specified wavelength within the emission wavelength range of the optical emitter emission from the fluorescent probe, if not stated otherwise. The first and second chambers may be filled with an optically transparent or translucent material, such as a mold material. However, the chambers could also not be filled with any material and only contain air. Furthermore, the chambers could also be filled with different materials, e.g. the first chamber could be filled with a mold material transparent to an emission wavelength of the optical emitter, the second chamber, however, could be filled with a number mold material which is transparent only to the Stokes shifted emission from the fluorescent probe and attenuates or blocks emission from the optical emitter. This way, the material has a filter function arranged for fluorescence detection.

The optical emitter is arranged in the first chamber and configured to emit through a first aperture in the housing. The optical emitter emits pulses of light at the specified wavelength. The specified wavelength is arranged to optically excite the fluorescent probe to be positioned in front of the sensor module. For example, the optical emitter comprises a light emitting diode or a laser diode. Furthermore, they may also be more than a single optical emitter implemented into the sensor module.

The detector is arranged in the second chamber. The detector is configured to detect light entering through a second aperture. For example, the detector is arranged to detect photons emitted by the fluorescent probe. In other words the detector is sensitive to a fluorescence emission from the fluorescent probe after the probe has been excited by the optical emitter. The detector may comprise a point-like detector such as a single photodiode or an array of more than a single detector such as an array of photodiodes, Furthermore, the detector may be an image detector such as a charge-coupled device, CCD, or a CMOS photo sensor.

The control unit is configured to initiate a modulated or pulsed emission of the optical emitter. The emission of the optical emitter typically is modulated, e.g. emission is pulsed or modulated by a continuous wave, such as a sinusoid or square wave. For example, the control unit generates trigger pulses of a control signal which initiate the optical emitter to emit one ore a plurality of sending pulses of electromagnetic radiation in response. Pulses may have a frequency in the kHz range, for example 80 kHz. In operation, the optical emitter emits light at the specified wavelength which illuminates a target outside the sensor module.

The sensor module further has a measurement block which is configured to determine respective difference values. The difference values are representative of an arrival time of received photons with respect to their corresponding emission pulses. In case the target comprises a fluorescent probe, molecules may be optically excited and, in turn, emit photons which eventually traverse back to the sensor module where they get detected by the detector. Thus, fluorescence can be excited by pulsed excitation, e.g. repetitively by short laser pulses. The time difference between excitation and emission is measured by the electronics of the sensor module that in a certain sense act like a stopwatch.

For example, the arrival time is defined by a time difference between a time instant when an emission pulse is emitted and a time instant when a received emission, such as a single photon, is detected. One time instant could be generated by the detector, e.g. by generating a timing signal every time a photon is detected. Another time instant may be provided to the measurement block by the control unit, e.g. by generating a timing signal every time a pulse is emitted. A difference signal can be derived from both timing signals and is a measure of the difference value and arrival time. The difference value may be provided as a digital value after appropriate digital conversion.

The histogram block is configured to accumulate the difference values into a histogram. For example, the histogram block comprises a plurality of addressable memory cells. An incoming difference value increments a histogram memory cell at its associated digital address, e.g. at the address the histogram block receives from the measurement block. Typically, the histogram block comprises fast digital logic, e.g. in the form of Field Programmable Gate Arrays (FPGA) or a microprocessor. Since the histogram block at some point also must be available for data readout, the histogram block may interrupt processing incoming data. This prevents continuous data collection. In order to be available for continued data acquisition the histogram block may comprise a switching circuit in order to select between two or more memory cells so that at least one is available for incoming data.

The processing unit combines several functions. First, the circuit is configured to compute one or more time-of-flight values based on an evaluation of the histogram. Second, a fluorescence lifetime value is computed by the processing circuit from one or more time-of-flight values computed from the histogram. Finally, an output signal is generated which is indicative of the fluorescence lifetime of the fluorescent probe. The output signal may be provide at an output terminal of the sensor module and can be communicated and processed by a fluorescence detection device.

One way to evaluate the histogram is to determine peaks in the histogram data representation. For example, the histogram may be organized with several bins, which e.g. are of equal size. A time distance between neighboring bins may correspond to a value of variation for the time periods between the trigger pulses. For example, if the time period is changed by one of such time distances, a detected aliased received photon will be sorted into one of the neighboring bins with respect to the previous aliased received pulse. Received photons emitted by an actual fluorescent probe will be sorted into the same bin in case their arrival time is the same. This accumulation of detected photons leads to a peak which determines a time-of-flight value. In turn, this time-of-flight value can be translated into a fluorescence lifetime.

Another way to evaluate the histogram is to determine a slope of peaks in the histogram data representation. For example, the histogram of photon arrivals per time bin represents the time decay one would have obtained from a "single shot" time-resolved analog recording. The slope can be determined by fitting a decay function, e.g. an exponential decay function, to the data collected in the histogram. A decay rate is an indication of the fluorescence lifetime. Finally, the output signal is generated by the processing unit to be a measure of the computed decay rate or fluorescence lifetime.

The proposed sensor module comprises components to perform fluorescence analysis such as time-correlated single photo counting in a single package. In fact, the sensor module includes the source, the detector and the data analysis in one package. The sensor module can be made small enough to fit into mobile devices like smartphones or tablets. Fluorescence analysis can be carried out as a mobile application without the need of bulky equipment. As a consequence the sensor module is less sensitive to optical misalignment and due to wafer level manufacturing can be made much less expensive. Thus, typical application of fluorescence principles is not restricted to research laboratories any longer. There are a number of application fields such as chemistry, physics, biology, microbiology and mobile healthcare including skin cancer detection. Other applications of the sensor module include imaging, autofocusing and fluorescence lifetime imaging microscopy (FLIM) that can be done with the same device.

Furthermore, the sensor module can also be used for time-of-flight (ToF) applications such as distance measurement. For example, a distance measurement can complement the detection of fluorescence information for calibration purposes. In fact, during a measurement mode of operation the fluorescence probe may be located in a known and constant distance with respect to the sensor module. However, in a time-of-flight mode of operation the sensor module could be set to compute from the difference values a time-of-flight value of light reflected at the target instead of fluorescence emission. The difference value can be translated into a distance value. In turn, the distance value can be used to compensate for a time offset in the fluorescence lifetime measurement.

In at least one embodiment the housing further comprises a cover section with a main surface. Optionally, the housing may be complemented with a cover plate arranged on the main surface. The cover plate could, however, be part of a device into which the optical sensor module may be implemented, a mobile phone or tablet, for example.

The housing could be arranged on a carrier such that the optical emitter is located inside the first chamber, the detector is located inside the second chamber but both are attached to the carrier. The main surface of the cover section is then located opposite to the carrier. The sensor module further comprises a couple of means for operating the optical emitter and detector as well as on-chip signal processing. The sensor module comprises a measurement block, a histogram block, a processing circuit and a control unit. These means could be arranged on the carrier or be integrated into the housing by other ways, such as molding.

In at least one embodiment the first and the second aperture both lie within an emission volume or emission cone of the optical emitter. Therein, the emission volume or cone includes all points in space that may, at least theoretically, be illuminated by the emitter, e.g. for a fixed emitter position and orientation within the optical sensor module.

In at least one embodiment the fluorescent probe is positioned within a field of view of the sensor module. The housing, the optical emitter and the detector are arranged with respect to each other such that at least a fraction of light to be emitted by the optical emitter excites the fluorescent probe. Furthermore, the arrangement is such that at least a fraction of fluorescent emission reaches the detector.

During operation the target including the fluorescence probe is positioned within the field of view of the sensor module. With each emitted pulse by the optical emitter the fluorescence probe can be optically excited to emit photons. Emission of photons is a random process but there is a chance for photons to traverse back to the sensor module and get detected by the detector. A fraction of fluorescent emission that reaches the detector can be analyzed and collected as a histogram. Finally, the histogram can be evaluated and a fluorescence lifetime can be determined.

In at least one embodiment an optical filter is arranged above or inside the second aperture. The optical filter is configured to pass only light which is spectrally shifted with respect to the specified wavelength. Furthermore, the optical filter may be fixed to the housing or, alternatively, maybe interchangeable. Furthermore, the optical filter could also be arranged on, at least parts, of the detector and/or optical emitter.

The optical filter is a means to separate excitation by the optical emitter from the fluorescence detected by the detector. Typically, fluorescence emission is red shifted according to the Stokes shift of molecules in the fluorescent probe. Thus, the optical filter may be an interference filter with a transmission which blocks the specified wavelength of excitation of the optical emitter and pass a wavelength range of the Stokes shifted fluorescence emission. Furthermore, there may also be competing fluorescence from other fluorophores. Using the optical filter allows for detecting specific fluorophores only.

In at least one embodiment the detector comprises a single photon avalanche diode, or SPAD for short. The detector may also comprise an array of SPADs.

In at least one embodiment the optical emitter comprises a vertical cavity surface emitting laser, or VCSEL for short. Alternatively, the optical emitter comprises a vertical external cavity surface emitting laser, VECSEL for short. Both lasers types are configured to emit light of one or more specified wavelengths. For example, emission can be pulsed or in a modulated continuous wave, such as a sinusoid or square wave. A VCSEL or VECSEL laser diode is able to provide picosecond pulses and supports integration into an integrated circuit.

In at least one embodiment the optical emitter is tunable within a range of operation. The control unit is further arranged to set the specified the wafer to add value from within the range of operation. Tuning allows to adjust excitation to a range of fluorescent probes. Furthermore, the sensor module can also be used for collecting fluorescence excitation spectra by swiping through the tunable range of excitation wavelengths.

In at least one embodiment one or more optical lenses are coupled to the first and/or second apertures. In addition or alternatively, the system of optical lenses can be coupled to the first and/or second apertures.

The lenses can be used for focusing light emitted by the optical emitter and/or one or more detector lenses for focusing light entering the second chamber. The lenses, however, may be arranged for creating an image on the detector, for example.

The lenses may be arranged in or near the apertures in the chambers. The emitter lens is arranged above, e.g. directly above, the optical emitter on a side of the housing facing the optical emitter, for example. For example, the emitter lens may cover the first aperture. The detector lens is arranged above, e.g. directly above, the detector on a side of the housing facing the detector, for example. The detector lens may cover the second aperture, for instance.

Furthermore, the lenses may constitute an optical systems, or be part of an optical system, to produce an image of the target having the fluorescence probe. This way the sensor module can be used for fluorescence imaging. The optical system could, for example, provide wide field imaging to collect a complete image at a time. However, the optical system can also be part of a scanning stage in order to collect an image in a stepwise fashion.

In at least one embodiment the measurement block comprises one or more time to digital converters, TDC for short. For example, the TDC comprises a single fully digital circuit that can measure time differences based on the delay times of signals in semiconductor logic gates or the conductor strips between them, i.e. the TDC is arranged to digitally determine respective difference values.

In at least one embodiment the histogram block comprises one or more memory cells which are connected to the one or more time-to-digital converters.

In at least one embodiment the processing circuit and/or the control unit comprises a microcontroller.

In at least one embodiment the measurement block, the histogram block, the processing circuit, the control unit and the detector are integrated into a single semiconductor die. This way these components are integrated into a common integrated circuit which may be arranged on a carrier or be embedded into the housing, e.g. by molding.

In at least one embodiment the optical emitter is integrated into the same single semiconductor. Typically, the light source, such as the VCSEL laser diode, is connected to said integrated circuit and the integrated circuit only comprises a dedicated driver circuit. Alternatively, the optical emitter is integrated into a separate semiconductor die which is electrically connected to the single semiconductor die. The single integrated circuit may also comprise the light source itself if this component can be integrated, by means of a CMOS process, for example.

In at least one embodiment a fluorescence detection device comprises a housing, an electronics board, a display unit and a sensor module.

The housing has a detection aperture. The electronics board is arranged in the housing and has a central processing unit. Typically, fluorescence detection device is a mobile device such as a smartphone or tablet. Thus, electronics board may have addition electronic components. The display unit is connected to the electronics board and attached to the housing. For example, the display unit is a touchscreen. The sensor module is arranged for determining a fluorescence lifetime along the aspects discussed above and described in accompanying claims. The sensor module is arranged in the housing behind the detection aperture.

In at least one embodiment the detection further comprises a lens, objective and/or a xy-scanning stage. For example, the lens is arranged in or one the detection aperture. The lens could be part of a camera system of the device such as the camera of a smartphone or tablet. However, the lens could also be part of an external system which can be arranged in front of the detection aperture. For example, a microscope add-on could comprise the lens such as a microscope objective lens and complement the fluorescence detection device with microscope functionality. Furthermore, the lens could be a scanning lens which is arranged to move its elements and thereby alter an optical path along x and y directions. An incident beam of light emitted by the optical emitter is varied with respect to the optical axis of the lens. By varying the angle of incidence a focal spot is caused to scan over a field of view in the image plane on the target.

Furthermore, the lens could be a wide field lens such as an objective or a microscope objective. Such a lens allows to image a wide field-of-view and collect fluorescence emission from various positions on the target. Another way to collect fluorescence emission from various positions is to use a xy-scanning stage coupled to the detection device. The stage is arranged to move the device (or parts thereof) relative to the fluorescent probe. Alternatively, the xy-scanning stage may be arranged to move the fluorescent probe relative to the device.

In at least one embodiment a method of determining a fluorescence lifetime comprises the steps discussed in the following. The method is executed using a sensor module comprising an opaque housing having a first chamber and a second chamber which are separated by a light barrier.

First, the fluorescent probe is positioned in front of the sensor module. A control unit initiates pulsed emission of the optical emitter which is arranged in the first chamber.

Emitted pulses leave the sensor module through a first aperture in the chamber.

The emitted pulses of light have a specified wavelength which is arranged to optically excite the fluorescent probe. Photons are emitted from the fluorescent probe and are received through a second aperture in the second chamber. The photos are detected using a detector which is arranged in the second chamber.

A measurement block determines respective difference values which are representative of an arrival time of one or more of the received photons with respect to the emission pulses. A histogram block is used to accumulate the difference values in a histogram which in succeeding steps is evaluated by means of a processing unit.

First, a time-of-flight value or several time-of-flight values are computed based on an evaluation of the histogram by means of the processing circuit. Second, a fluorescence lifetime is computed from the time-of-flight values. Finally, an output signal is generated which is indicative of the fluorescence lifetime of the fluorescent probe.

In addition, the evaluation may also be complemented by measuring a distance between the sensor module and the fluorescent probe. This could be accomplished simply by positioning the fluorescent probe at a known and constant distance. Then, the computed time-of-flight values are calibrated to this particular distance. However, distance can also be measured by the same sensor module. The light emitted by the optical emitter may lead to reflection (at the same wavelength) and can be distinguished from fluorescence emission by the fluorescent probe. Reflected light gives rise to difference values and corresponding time-of-flight values. Instead of calculating a lifetime, however, these time-of-flight values can be translated into a distance value instead. This way it is possible to calibrate fluorescence lifetimes at varying distances.

In at least one embodiment a fluorescence images generated from several fluorescence lifetime measurements. For example, the fluorescent probe is positioned at several different positions with respect to the sensor module. Based on generating respective output signals which are each indicative of the fluorescence lifetime of the fluorescent probe at the particular position the fluorescence image is constructed as a function of said positions.

In the following, the concept presented above is described in further detail with respect to drawings, in which exemplary embodiments are presented.

In the exemplary embodiments and Figures below, similar or identical elements may each be provided with the same reference numerals. The elements illustrated in the drawings and their size relationships among one another, however, should not be regarded as true to scale. Rather individual elements, such as layers, components, and regions, may be exaggerated to enable better illustration or improved understanding.

DETAILED DESCRIPTION

Figure 1:
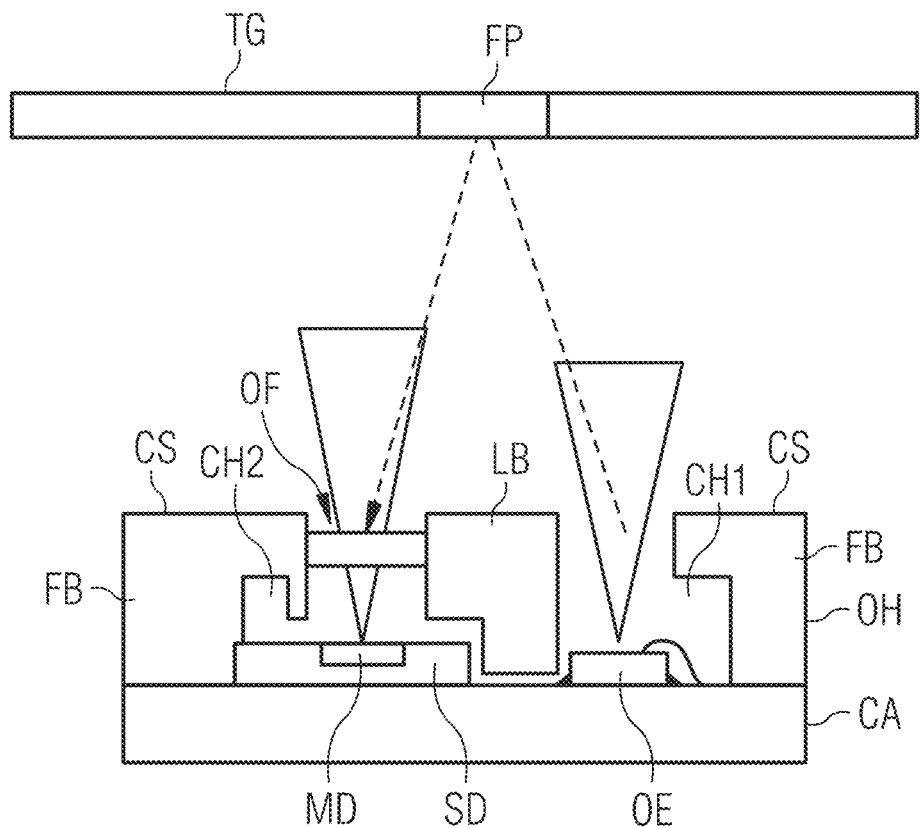
FIG. 1 shows an exemplary embodiment of a fluorescence lifetime sensor module.

FIG. 1 shows an exemplary embodiment of a fluorescence lifetime sensor module. The sensor module (shown in side view) comprises a carrier CA and an opaque housing OH arranged on the carrier. The housing comprises a light barrier LB which divides the housing into a first and a second chamber CH1, CH2. The first and second chambers CH1, CH2 are further confined laterally by a frame body FB arranged in the housing. A cover section CS is located opposite to the carrier CA and thereby covers the chambers CH1, CH2. The cover section CS, frame body FB, and light barrier LB are manufactured by a continuous piece of material, such as a mold material, for example. The carrier CA provides mechanical support and electrical connectivity to electronic components integrated into the sensor module. For example, in this embodiment the carrier CA comprises a printed circuit board, PCB (not shown). However, in other embodiments (not shown) the carrier CA can also be part of the housing and electronic components are embedded into the housing by molding for example.

An optical emitter EM is located inside the first chamber CH1. The optical emitter OE is arranged on and electrically connected to the carrier CA, e.g. to the PCB. The optical emitter OE is a laser diode, such as a VCSEL or VECSEL. These types of lasers are configured to emit light at a specified wavelength, e.g. in the UV, visual or infrared part of the electromagnetic spectrum. In this particular embodiment the optical emitter OE is tunable to emit at a specified wavelength. The specified emission wavelength, or an emission spectrum, lies in the IR or UV/vis. For example, vertical-cavity surface-emitting lasers, VCSEL, or vertical-external-cavity surface-emitting-lasers, VECSEL, predominantly emit in the IR, e.g. at 940 nm.

A detector MD is arranged inside the second chamber CH2 and on the carrier CA. In this particular embodiment, the detector MD is integrated into a single semiconductor die SD together with other electronics discussed further below. The detector MD comprises a SPAD array which is sensitive to single photons.

First and second apertures AP1, AP2 are arranged into the cover section CS. The first and the second apertures AP1, AP2 are positioned above the optical emitter OM and the main detector MD, respectively. In fact, the apertures AP1, AP2 lie within an emission cone of the optical emitter OE and a field of view of the detector MD, respectively. Therein, the emission cone includes all points in space that may, at least theoretically, be illuminated by the optical emitter OE, e.g. for a fixed emitter position and orientation within the sensor module. Similarly, the field of view of the detector MD includes all points in space from where, at least theoretically, light after reflection at an external target TG may traverse towards the detector MD, e.g. for a fixed detector position and orientation within the optical sensor module.

Furthermore, an optical filter OF is arranged in the second aperture AP2 above the detector MD. Typically, the optical filter has a transmission characteristic which blocks or at least attenuates at the specified wavelength of the optical emitter. This way the detector is prevented from overflow by the relatively high emission intensity of the optical emitter. Furthermore, the transmission is arranged to pass light which is red shifted with respect to the specified emission wavelength of the optical emitter. Upon excitation, the fluorescent probe will emit light at a longer wavelength than that of the excitation light. The fluorescence light is filtered out against scattered excitation light or background BG by means of the optical filter OF. The optical filter may be an interference filter such as an optical cut-off filter, bandpass, long or short pass filter. Typically, the passband is chosen with respect to the fluorescence probe to be studied and the optical filter passes light having a wavelength corresponding to the fluorescence emission of the probe. Optionally, in one of the apertures or both of them a neutral density filter can be arranged and is used to attenuate the light levels to maintain a single photon statistics at the detector.

Operation will be discussed in detail in the following Figures. Briefly, however, the sensor module is positioned with respect to a target TG carrying a fluorescent probe FP.

The optical emitter OE emits light into its emission cone and towards the probe. The mission light the optical emitter triggers a timing of electronics to generate a timing signal or start signal indicates the start of the emission. The emission by the optical emitter excites fluorescent molecules in the probe which, in turn, undergo transitions to the excited states. When decaying back from the states to the ground states they emitter photon of a longer wavelength. Another timing signal or stop signal is triggered when these emitted photons are detected by the detector. The time difference between the start and stop timing signals is evaluated by a measurement block MB and difference values are calculated which at an output to pay histogram block HIST. A processing circuit PRC evaluates the histogram and derives time of flight values which are indicative of the time period starting with the emission and ending with the detection. These time of flight values are indicative of a fluorescence lifetime of the fluorescent probe.

Figure 2:
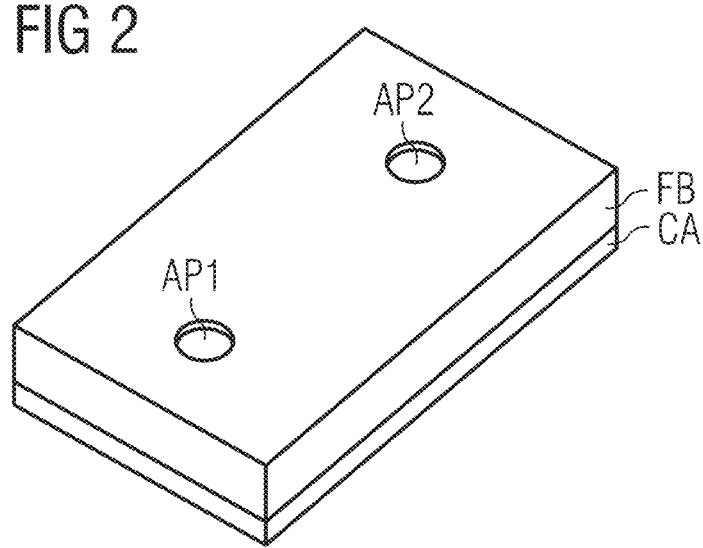
FIG. 2 shows an exemplary embodiment of a fluorescence lifetime sensor module.

FIG. 2 shows an exemplary embodiment of a fluorescence lifetime sensor module. The sensor module is shown in perspective view. The opaque housing OH including frame body FB is arranged on a carrier CA and comprises all components necessary to implement a fluorescence detection system including the optical emitter as light source, the detector and data analysis system in one small package. An exemplary package size is about 4 mm×2.5 mm×1 mm. Furthermore, the drawing shows apertures AP1 and AP2 in the housing to facilitate emission and detection by the sensor module.

Figure 3:
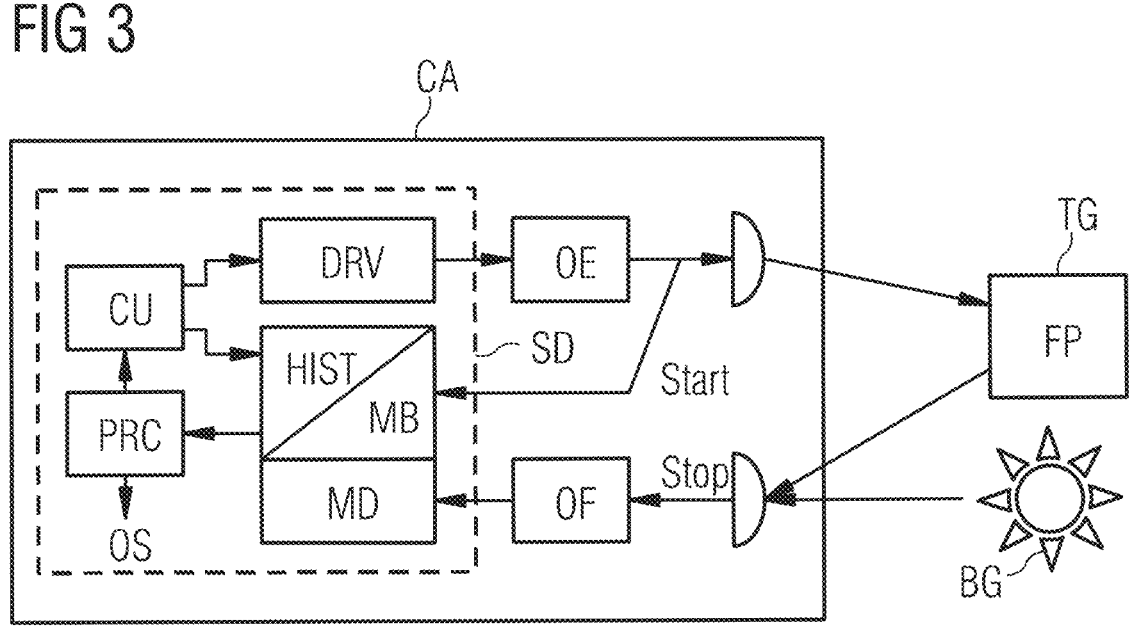
FIG. 3 shows an exemplary block diagram of a fluorescence lifetime sensor module.

FIG. 3 shows an exemplary block diagram of a fluorescence lifetime sensor module. The components shown in the diagram of all arranged and electrically connected to the carrier CA, for example a printed circuit board. The semiconductor die SD comprises an integrated circuit. The integrated circuit comprises a control unit CU, a driver unit DRV, the detector MD and preprocessing components such as a measurement block MB and a histogram block HIST, and, further, a processing circuit PRC.

The control unit CU initiates or triggers emission of the optical emitter OE. For example, the control unit generates trigger pulses of a control signal which initiate the optical emitter to emit one ore a plurality of sending pulses of electromagnetic radiation in response. The trigger pulses of a control signal are provided to the driver unit DRV which has an interface to the optical emitter OE, such as a VCSEL laser diode, and allows digital control of the modulation and bias currents, for example. The emission of the optical emitter OE typically is modulated, e.g. emission is pulsed or modulated by a continuous wave, such as a sinusoid or square wave. For example, pulses may have a frequency in the kHz range, for example 80 kHz. The control signal is also sent to the measurement block MB, e.g. by generating a timing signal every time the control unit CU triggers pulsed emission of the optical emitter OE.

In response to the trigger pulses of a control signal of the control unit CU the driver unit DRV drives the optical emitter OE. Emission by the optical emitter is focused by lens L1 and directed to the target TG and excites fluorescence emission in fluorescent probe FP. Photons emitted by the probe may traverse back to the sensor module and enter the module via another lens L2 and optical filter OF. Every time every time a photon is detected the detector generates a timing signal which is provided to the measurement block MB and used for determining a fluorescence lifetime.

For example, an arrival time is defined by a time difference between a time instant when an emission pulse is emitted and a time instant when a received emission, such as a single photon, is detected. The measurement block MB receives both timing signals indicating start of emission and stop of detection and derives a difference signal from both timing signals. The difference signal is a measure of a difference value and arrival time. The measurement block MB comprises one or more time-to-digital converters which convert the timing signals or difference signal into a digital value difference value.

The difference values are output to the histogram block HIST and accumulated into a histogram. Bins of the histogram have a fixed time width $t_{fix}$. Difference values that correspond to arrival times within $t+t_{fix}$ are plotted in one specific bin etc. For this purpose the histogram block comprises a plurality of addressable memory cells. An incoming difference value increments a histogram memory cell at its associated digital address, i.e. the address provided by the time-to-digital converter.

Further data analysis is done by the processing circuit PRC. In this particular embodiment the processing circuit comprises a microcontroller which is programmed to perform a number of processing steps. Basically, the microcontroller is configured to compute time-of-flight values based on an evaluation of the histogram. These time-of-flight values are then computed into a fluorescence lifetime. The microcontroller generates an output signal OS which is indicative of the fluorescence lifetime of the fluorescent probe FP. Details of the data analysis will discussed with respect to FIG. 4.

The output signal OS can be used to create a fluorescence image. For example, mobile devices such as smartphones and tablets are typically equipped with a high resolution camera system. The processing circuit PRC or a processor of the mobile device can be arranged to overlap or matched a picture taken by the mobile device with the output signal of the sensor module. This results in a fluorescence map which can be outputted on a display of the mobile device, for example. In order to collect output signals from different positions on the target the sensor module can be combined with a scanning lens a wide field lens such as an objective. A xy-scanning stage can move the mobile device (or parts thereof) relative to the fluorescent probe. Alternatively, the xy-scanning stage may move the fluorescent probe relative to the device in order to collect data, i.e. output signals OS from different positions. Based on generating respective output signals OS at the particular position the fluorescence image is constructed as a function of the positions.

Figure 4:
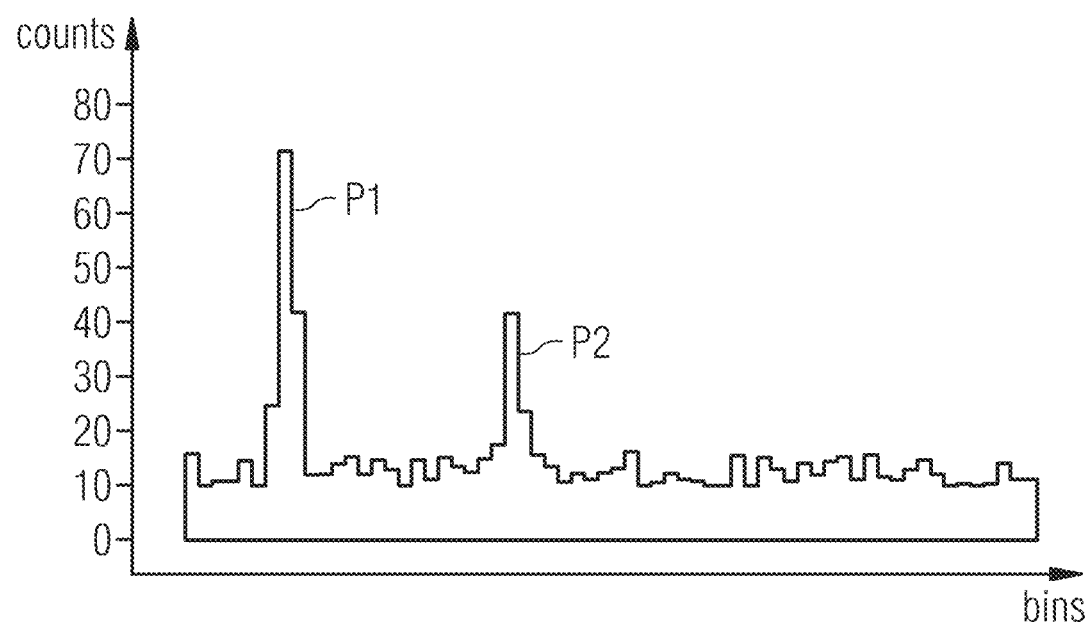
FIG. 4 shows an exemplary histogram for determining a fluorescence lifetime with a fluorescence lifetime sensor module.

FIG. 4 shows an exemplary histogram for determining a fluorescence lifetime with a fluorescence lifetime sensor module. The histogram accumulates difference values which result from cycles of an emission pulse by the optical emitter and corresponding detection of fluorescence emission by the detector. The digital timing result is represented by the difference values and then used to address the histogram memory so that each possible difference value corresponds to a memory cell or histogram bin of fixed time width $t_{fix}$. The addressed histogram cell is incremented with each detection event. When sufficient counts have been collected, the histogram memory can be read out. The histogram data can then be used for display and data analysis, i.e. fluorescence lifetime calculation.

The exemplary histogram shows two peaks P1 and P2 which correspond to two different fluorescence lifetime values. The positions of the peaks determines a time-of-flight value. In turn, this time-of-flight value can be translated into a fluorescence lifetime. With higher time resolution slope of peaks can be determined in the histogram representation. The slope can be determined by fitting a decay function, e.g. an exponential decay function, to the data collected in the histogram. A decay rate is the inverse of the fluorescence lifetime.

The proposed method for determining a fluorescence lifetime is based on a time of flight measurement. As such the method depends also on the distance between the sensor module and the target with the fluorescent probe. As a consequence determined fluorescence lifetime of values may only be comparable when collected at the same, constant distance. Fluorescence lifetime measurements in different distances may need to be calibrated with an offset.

There are several ways to achieve comparable lifetime measurements. First, during one or more of fluorescence lifetime measurements the distance can simply be kept constant. This could be achieved, for example, by choosing a xy-scanning stage to either move the fluorescent probe or the sensor module. Second, typically either the sensor module or the fluorescence detection device are equipped with one or more lenses such as a microscope objective or a scanning objective. These lenses have a defined focal length and, thus, the probe can be focused to a defined focus spot. When in focus, a defined distance for the fluorescence lifetime measurement is also established. Finally, the proposed sensor module can also be used as a time of flight measurement device. Instead of recording fluorescence emission the device could also record reflected light from the optical emitter. Using the same circuitry that reflected light would also give rise to an arrival time which can be translated into a time of flight value as well. Such a time of flight value is a function of distance and can thus be used as an offset to calibrate the fluorescence lifetime measurement.

Figure 5A:
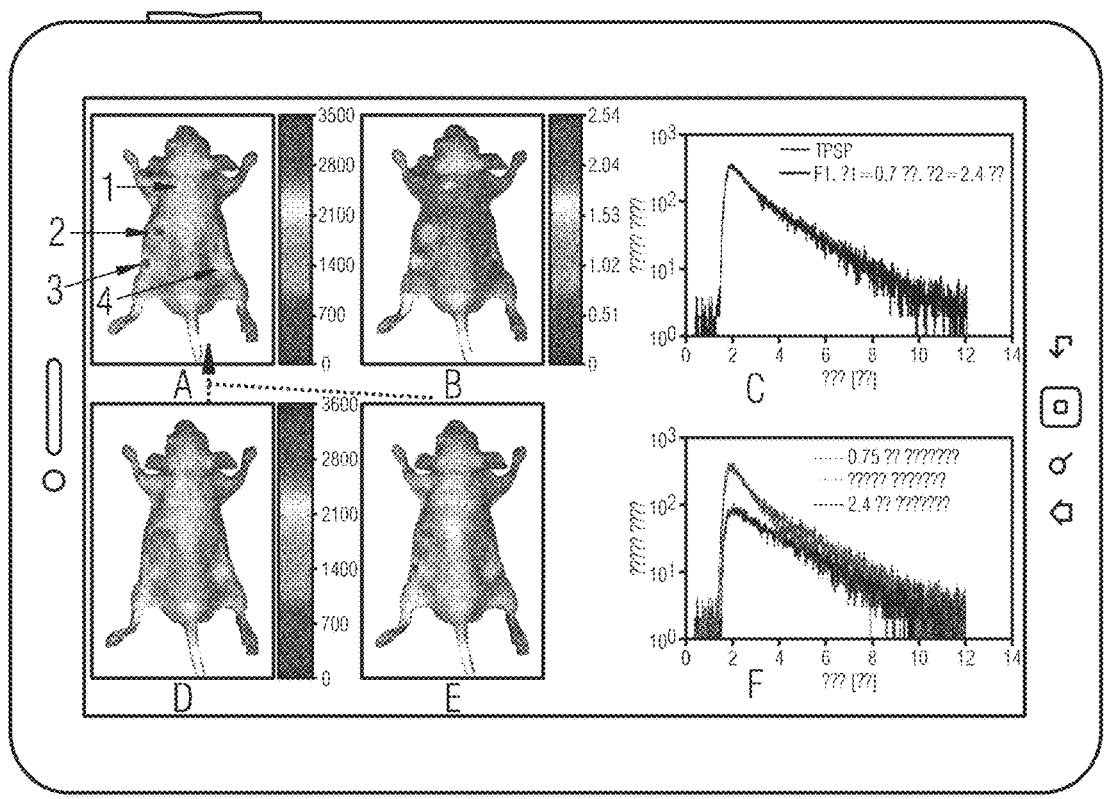
FIGS. 5A, 5B show exemplary mobile devices having a fluorescence lifetime sensor module.
Figure 5B:
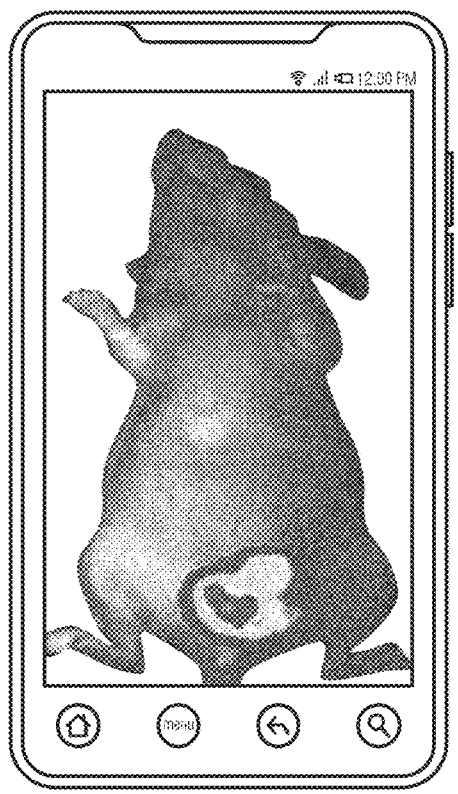

FIG. 5A and FIG. 5B show exemplary mobile devices having a fluorescence lifetime sensor module. The mobile device is a tablet (see FIG. 5A) or a smartphone (see FIG. 5B), for example. Both devices comprise a housing, an electronics board, a display unit and a sensor module. For example, the sensor module is arranged in the housing behind the detection aperture. A camera and optics integrated into the mobile device can be used to combine a picture taken by the mobile device with fluorescence lifetime data collected by the sensor module. Imaging allows for producing an image based on the differences in lifetime or decay rates of the fluorescence from a fluorescent probe. Thus, the mobile device can be used for mobile fluorescence-lifetime imaging microscopy or FLIM.

The invention claimed is:

1. A fluorescence lifetime sensor module comprising:
an opaque housing having a first chamber and a second chamber separated by a light barrier,
an optical emitter arranged in the first chamber, and configured to emit through a first aperture pulses of light of a specified wavelength arranged to optically excite a fluorescent probe positioned in front of the sensor module,
a detector arranged in the second chamber, and configured to detect through a second aperture received photons from the fluorescent probe, wherein the received photons comprise:
first photons corresponding to a reflection of at least some of the pulses of light by the fluorescent probe, and
second photons corresponding to an a fluorescent emission by the fluorescent probe in response to an excitation of the florescent probe by the pulses of light,
a measurement block comprising one or more time-to-digital converters, wherein the measurement block is configured to determine respective difference values representative of an arrival time of one of the received photons with respect to the emission pulses and,
a histogram block comprising one or more memory cells, wherein the histogram block is configured to accumulate the difference values in a histogram,
a processing circuit configured to operate in a time-of-flight mode of operation and in a measurement mode of operation,
wherein in the time-of-flight mode of operation, the processing circuit is configured to:
determine, based on the difference values, first time-of-flight values corresponding to the first photons, and
determine, based on the first time-of-flight values, a distance between the sensor module and the fluorescent probe, and
wherein in the measurement mode of operation, the processing circuit is configured to:
compute second time-of-flight values for the second photons based on an evaluation of the histogram,
compute a time offset value based on the determined distance between the sensor module and the fluorescent probe,
compute a fluorescence lifetime based on the second time-of-flight values and the time offset value, and
generate an output signal being indicative of the fluorescence lifetime of the fluorescent probe, and a control unit configured to initiate pulsed emission of the optical emitter.

2. The sensor module according to claim 1, wherein
the fluorescent probe is positioned within a field of view of the sensor module,
the housing, the optical emitter and the main detector are arranged with respect to each other such that at least a fraction of light to be emitted by the optical emitter excites the fluorescent probe to produce the fluorescent emission, and such that at least a fraction of the fluorescent emission reaches the detector.

3. The sensor module according to claim 1, wherein
an optical filter is arranged above or inside the second aperture, and is configured to pass only light which is spectrally shifted with respect to the specified wavelength and
the optical filter is fixed to the housing or interchangeable.

4. The sensor module according to claim 1, wherein
the main detector comprises a single-photon avalanche diode, SPAD, or an array of SPADs, and/or
the optical emitter comprises a vertical-cavity surface-emitting laser, VCSEL, or a vertical-external-cavity surface-emitting-laser, VECSEL, configured to emit light.

5. The sensor module according to claim 1, wherein the optical emitter is tunable within a range of operation and the control unit is arranged to set the specified wavelength to a value from within the range of operation.

6. The sensor module according to claim 1, wherein one or more optical lenses or a system of optical lenses is coupled to the first and/or second apertures.

7. The sensor module according to claim 1, wherein the one or more memory cells are connected to the one or more time-to-digital converters.

8. The sensor module according to claim 1, wherein the processing circuit and/or control unit comprises a microcontroller.

9. The sensor module according to claim 1, wherein the measurement block, the histogram block, processing circuit, the control unit and the detector are integrated into a single semiconductor die.

10. The sensor module according to claim 9, wherein the optical emitter:
is integrated into the same single semiconductor, or
comprises a separate semiconductor die electrically connected to the single semiconductor die.

11. The sensor module according to claim 1 further comprising a carrier, wherein:
the opaque housing is arranged on the carrier and the housing comprises the light barrier,
the first and second chambers are further confined laterally by a frame body (FB) arranged in the housing,
a cover section is located opposite to the carrier and covers the chambers, and
the cover section, frame body, and light barrier are manufactured by a continuous piece of material or a continuous piece of mold material.

12. A fluorescence detection device comprising:
a housing having an detection aperture,
an electronics board arranged in the housing and having a central processing unit,
a display unit connected to the electronics board and attached to the housing, and
a sensor module according to claim 1 arranged in the housing behind the detection aperture.

13. The detection device according to claim 12, further comprising at least one of:
a lens arranged in or one the detection aperture, and/or configured as a scanning lens and/or a wide field lens, or
a xy-scanning stage coupled to the detection device and arranged to move the device or fluorescent probe relative to the fluorescent probe or relative to the device, respectively.

14. A method of determining a fluorescence lifetime using a sensor module comprising an opaque housing having a first chamber and a second chamber separated by a light barrier, the method comprising the steps of:
positioning a fluorescent probe in front of the sensor module,
initiating pulsed emission of the optical emitter using a control unit,
emitting pulses of light of a specified wavelength arranged to optically excite the fluorescent probe through the first aperture and using an optical emitter arranged in the first chamber,
detecting received photons from the fluorescent probe through the second aperture and using a detector arranged in the second chamber, wherein the received photons comprise:
first photons corresponding to a reflection of at least some of the pulses of light by the fluorescent probe, and
second photons corresponding to an a fluorescent emission by the fluorescent probe in response to an excitation of the florescent probe by the pulses of light
determining respective difference values representative of an arrival time of one of the received photons with respect to the emission pulses using a measurement block comprising one or more time-to-digital converters,
accumulating the difference values in a histogram using a histogram block comprising one or more memory cells, and
using a processing circuit:
determining, based on the difference values, first time-of-flight values corresponding to the first photons,
determining, based on the first time-of-flight values, a distance between the sensor module and the fluorescent probe,
computing second time-of-flight values based on an evaluation of the histogram,
computing a time offset value based on the determined distance between the sensor module and the fluorescent probe,
computing a fluorescence lifetime based on the second time-of-flight values and the time offset value, and
generating an output signal being indicative of the fluorescence lifetime of the fluorescent probe.

15. A method according to claim 14, wherein a fluorescence image is generated by positioning the fluorescent probe at several different positions with respect to the sensor module and based on generating respective output signals indicative of the fluorescence lifetime of the fluorescent probe at said positions.

* * * * *